United States Patent [19]
Robins et al.

[11] Patent Number: 4,650,561
[45] Date of Patent: Mar. 17, 1987

[54] GAS SENSOR

[75] Inventors: Ian Robins; John F. Ross, both of Hayes; Brian C. Webb, Sunbury-on-Thames, all of England

[73] Assignee: EMI Limited, Hayes, England

[21] Appl. No.: 751,146

[22] Filed: Jul. 2, 1985

[30] Foreign Application Priority Data

Jul. 4, 1984 [GB] United Kingdom ............... 8416994

[51] Int. Cl.⁴ .............................................. G01N 27/46
[52] U.S. Cl. ................................... 204/416; 204/419; 204/1 T; 357/25; 29/571
[58] Field of Search ................... 204/1 N, 416, 419; 357/25

[56] References Cited

U.S. PATENT DOCUMENTS

| | | | |
|---|---|---|---|
| 4,180,771 | 12/1979 | Guckel | 357/25 |
| 4,218,298 | 8/1980 | Shimada et al. | 204/419 |
| 4,269,682 | 5/1981 | Yano et al. | 204/419 |
| 4,305,802 | 12/1981 | Koshiishi | 204/419 |
| 4,397,714 | 8/1983 | Janata et al. | 357/25 |
| 4,437,969 | 3/1984 | Covington et al. | 357/25 |
| 4,502,938 | 3/1985 | Covington et al. | 204/419 |
| 4,505,799 | 3/1985 | Baxter | 357/25 |
| 4,508,613 | 4/1985 | Busta et al. | 204/419 |
| 4,512,870 | 4/1985 | Kohara et al. | 204/419 |
| 4,514,263 | 4/1985 | Janata | 357/25 |

FOREIGN PATENT DOCUMENTS 1520456 9/1975 United Kingdom .

Primary Examiner—Terryence Chapman
Attorney, Agent, or Firm—Fleit, Jacobson, Cohn & Price

[57] ABSTRACT

An ammonia gas sensor comprises a dual gate field effect transistor (FET) in which the two gate electrodes are of platinum deposited respectively by sputtering and evaporation. The gate regions of the two FETs are connected together differentially and the net drain source voltage represents the concentration of ammonia gas to which the sensor is exposed.

3 Claims, 3 Drawing Figures

GAS SENSOR

This invention relates to a gas sensor and it relates especially to an ammonia gas sensor.

An increasing need has arisen for a specific ammonia gas sensor capable of detecting ammonia gas particularly in the concentration range 1 to 1000 vpm.

British Pat. No. 1 520 456 describes a gas sensor in the form of a platinum gate field effect transistor. Although this device can be used to detect ammonia gas it is also sensitive to other gases containing atomic hydrogen, e.g. $H_2$, $H_2S$, and $CH_4$ which may be of litte inherent interest and may mask any response due to ammonia gas.

It is an object of the present invention to provide a device selective of ammonia gas.

Accordingly there is provided a field effect device sensitive to gaseous ammonia wherein a substrate of a semiconductor material of one polarity type has first and second gate regions, each interconnecting a drain region and a source region of the other polarity type, and respective gate electrodes of platinum are spaced apart from said first and second gate regions by an electrically insulating material on the substrate, said gate electrodes being desposited by evaporation and by sputtering respectively whereby electrical conduction in said first and second gate regions, when connected together differentially, depends on the concentration of ammonia gas, and is substantially independent of the concentration of other gases including hydrogen, to which the device is exposed.

The inventors have discovered that the sensitivity of a platinum gate field effect transistor to ammonia gas depends critically on the technique adopted to deposit the gate electrode-if the gate electrode is deposited by evaporation, the sensitivity of the device to ammonia gas is significantly higher than if the gate electrode is deposited by sputtering and whereas the evaporated layer is non-continuous, the sputtered layer tends to be continuous. Sensitivity to other gases (e.g. $H_2$, $H_2S$, $CH_4$) does not appear to depend on the deposition technique used. A differential arrangement of the above-defined kind operates as a specific ammonia gas sensor.

BRIEF DESCRIPTION OF THE DRAWINGS

In order that the invention may be carried readily into effect a specific embodiment thereof is now described, by way of example only, by reference to the accompanying drawings of which:

FIG. 1b shows a sectional view through the device along the line XY in FIG. 1a.

British Pat. No. 1 520 456 describes a gas sensor in the form of a platinum gate field effect transistor. For a given drain-source current ($I_{DS}$) the gate-source voltage ($V_{GS}$) depends on the concentration of hydrogen gas, or a gas containing atomic hydrogen (e.g. ammonia gas, hydrogen sulphide or methane), to which the sensor is exposed.

Contrary to expectation, the inventors have discovered that the sensitivity of a platinum gate field effect transistor to ammonia gas depends critically on the porosity and the technique adopted to deposit the gate electrode. More specifically, the inventors find that if the gate electrode is deposited by evaporation, the sensitivity of the device to ammonia gas is significantly higher than if the gate electrode is deposited by sputtering. In contrast, sensitivity to other gases (e.g. $H_2$, $H_2S$, $CH_4$) does not appear to depend on the deposition technique used.

This discovery is exploited in the present invention to provide a device selective of ammonia gas. The device comprises, in effect, two platinum gate field effect transistors which share a common substrate. The gate electrode of one of the field effect transistors, hereinafter referred to as the reference FET is formed by sputtering whereas the gate electrode of the other field effect transistor, hereinafter referred to as the measurement FET, is formed by evaporation and, as such, exhibits a significantly greater response to ammonia gas. The drain and source electrodes of the two FETs can be coupled differentially. In these circumstances, if the device is exposed to a gas other than ammonia gas (e.g. $H_2$, $H_2S$, $CH_4$) voltages developed across the drain source channels of the FETs have substantially the same magnitude but are in opposite senses and therefore cancel. If, on the other hand, the device is exposed to ammonia gas voltages of substantially different magnitude develop and the overall response characteristic, that is to say the net drain-source voltage, represents the concentration of ammonia gas to which the device is exposed. Thus, a dual gate device of the kind described, when operating differentially, functions as a specific ammonia gas sensor.

Figure 1A:
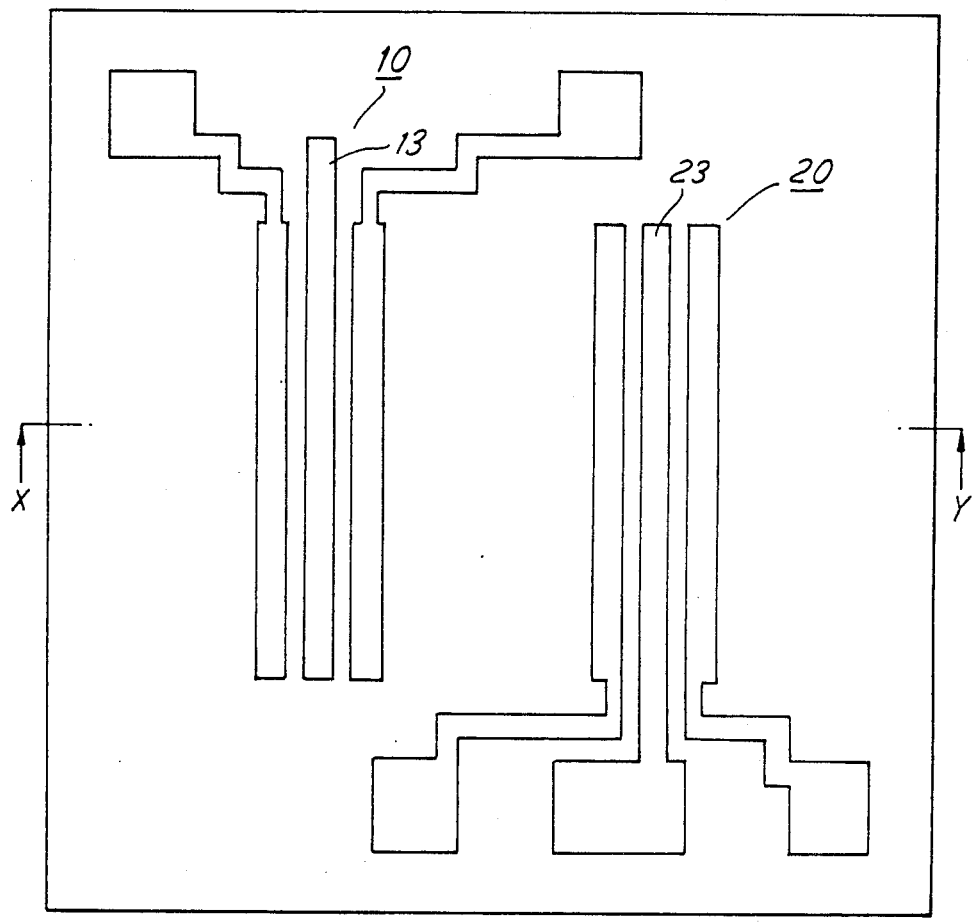
FIG. 1a shows a plan view of a dual gate device constructed in accordance with the invention.
Figure 1B:
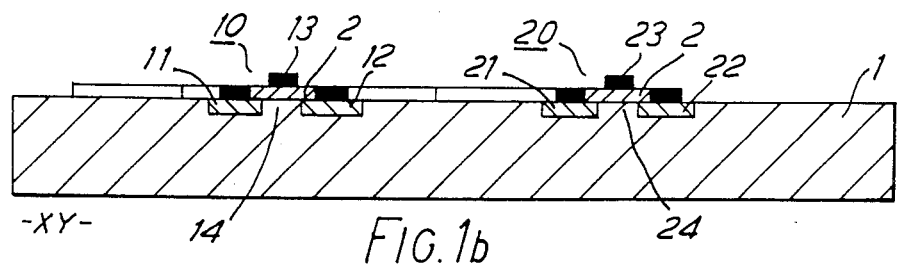

An example of a device, constructed in accordance with the present invention, is shown in the plan and sectional view of FIGS. 1a and 1b. The device comprises, in effect, two field effect transistors, namely a reference FET, shown generally at 10 and a measurement FET, shown generally at 20. The FETs share a common substrate 1 of p-type semi-conductor material (e.g. silicon) and have respective drain and source regions (11, 12; 21, 22) of the opposite (n) polarity type. The drain and source regions are provided with respective electrodes of a suitable metal e.g. Cr/Au or Al.

Each FET has a platinum gate electrode (13,23) overlying a respective gate region (generally shown at 14 and 24) which interconnects the drain and source regions and across which electrical conduction can take plate. The gate electrodes are spaced apart from the substrate 1 by an electrically insulating layer 2-typically of silicon dioxide, silicon oxynitride or silicon nitride.

As described hereinbefore, gate electrode 13 of the reference FET 10 is deposited by sputtering, whereas the gate electrode 23 of the measurement FET 20 is deposited by evaporation and as such exhibits a significantly greater response to ammonia gas. The evaporation and sputtering techniques used to deposit the gate electrodes are well known in the art and need not be described in detail. It has been found, by SEM analysis, that electrodes deposited by evaporation and sputtering exhibit markedly different film morphology; electrodes deposited by sputtering are found to have a greater surface smoothness than do electrodes deposited by evaporation. It is this difference in film morphology which is believed to be responsible for the different sensitivities to ammonia gas.

It will be appreciated that although, in the above-described example, the substrate 1 is of a p-type material and the drain and source regions are of a n-type material this need not necessarily be the case; in an alternative example, the polarity types may be reversed. Furthermore, the device described in relation to FIGS. 1a and 1b comprise, in effect, two FETs (10,20) having respective drain and source regions; alternatively, however, the two FETs could share a common source region or a common drain region.

Figure 2:
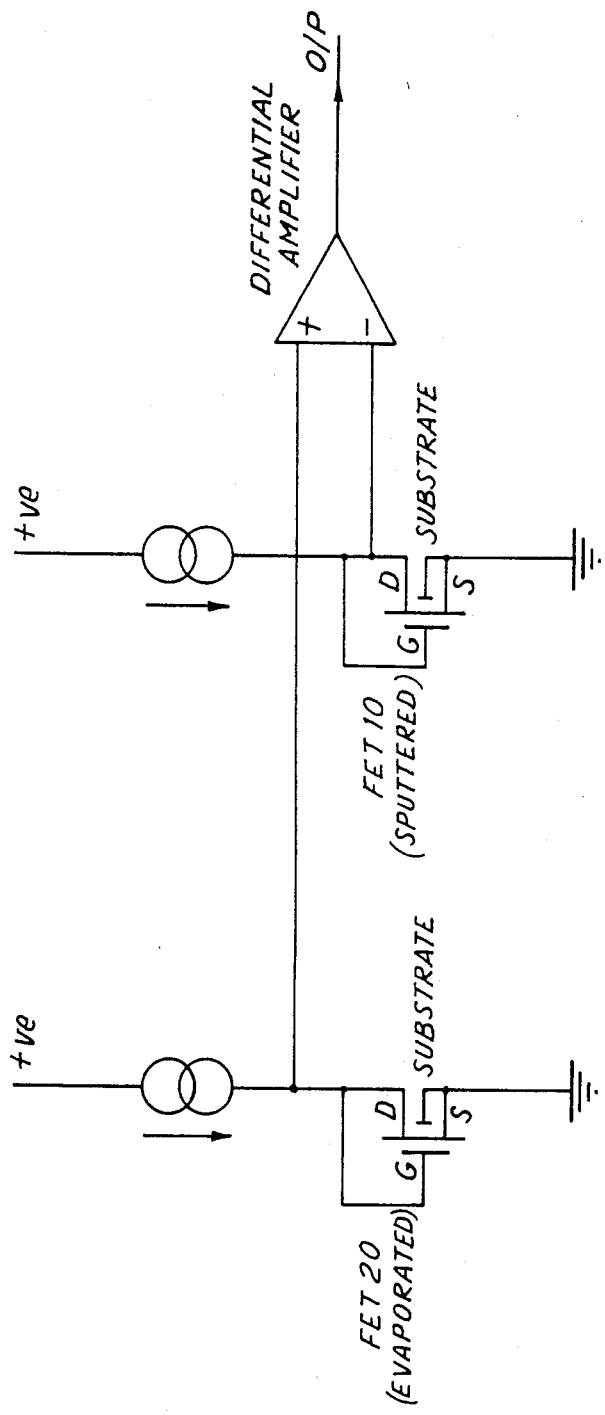
FIG. 2 shows a circuit for use with the device.

As explained hereinbefore, by differentially processing the voltages obtained at the drain electrodes of the two FETs, using a circuit of the kind shown in FIG. 2, the device functions as a selective ammonia gas sensor. The sensor also have on-chip heating and temperature control.

A dual gate device of this kind is particularly beneficial. Since both gate electrodes are of platinum the threshold voltages of both FETs should be the same. Moreover, since the FETs share a common substrate, and operate differentially, unwanted effects due to long term drift, temperature changes, and ageing should be greatly reduced.

We claim:

1. A field effect device sensitive to gaseous ammonia wherein a substrate of a semiconductor material of one polarity type, selected from p-type and n-type, has first and second gate regions each interconnecting a drain region and a source region of a polarity type opposite to said one polarity type, and respective gate electrodes of platinum are spaced apart from said first and second gate regions by an electrically insulative material on the substrate, said first and second gate electrodes being deposited by evaporation and by sputtering respectively whereby electrical conduction in said first and second gate regions, when coupled together differentially, depends on the concentration of ammonia gas, and is substantially independent of the concentration of other hydrogen-containing gases, to which the device is exposed.

2. A field effect device according to claim 1 wherein said first and second gate regions interconnect a common source region and respective drain regions.

3. A field effect device according to claim 1 wherein said first and second gate regions interconnect a common drain region and respective source regions.

* * * * *